US007448583B2

(12) United States Patent
Kim et al.

(10) Patent No.: US 7,448,583 B2

(45) Date of Patent: Nov. 11, 2008

(54) SUPPORTING DEVICE FOR A MONITOR FOR USE IN AN ULTRASONIC DIAGNOSTIC APPARATUS

(75) Inventors: Ghi Young Kim, Anyang-si (KR); Sun Ki Lee, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 0 days.

(21) Appl. No.: 11/368,476

(22) Filed: Mar. 7, 2006

(65) Prior Publication Data

US 2007/0023598 A1 Feb. 1, 2007

(30) Foreign Application Priority Data

Jul. 29, 2005 (KR) ..................... 10-2005-0069258

(51) Int. Cl.
*E04G 3/00* (2006.01)

(52) U.S. Cl. .................. 248/278.1; 248/284.1; 248/917

(58) Field of Classification Search ......... 248/917–922, 248/309.1, 176.1; 361/681
See application file for complete search history.

(56) References Cited

U.S. PATENT DOCUMENTS 5,812,368 A * 9/1998 Chen et al. .................. 361/681
6,015,120 A * 1/2000 Sweere et al. .......... 248/123.11
6,347,433 B1 * 2/2002 Novin et al. .................. 16/367
6,378,830 B1 * 4/2002 Lu .......................... 248/278.1
6,695,274 B1 2/2004 Chiu
6,769,657 B1 * 8/2004 Huang ..................... 248/278.1
7,177,144 B2 * 2/2007 Ha et al. ..................... 361/681
2003/0227739 A1 * 12/2003 Kim et al. ................... 361/681

* cited by examiner

*Primary Examiner*—Amy J. Sterling
(74) *Attorney, Agent, or Firm*—Oblon, Spivak, McClelland, Maier & Neustadt, P.C.

(57) ABSTRACT

The present invention relates to a support device for a monitor for use in an ultrasonic diagnostic apparatus, which enables a user to displace a monitor easily and diversely according to his or her posture, thereby providing convenience in use. The support device comprises: a base frame rotatably mounted to the main body; a pair of arms hingedly jointed to the base frame at respective one ends thereof; a connecting member for interlocking the pair of arms, the connecting member being hingedly coupled to the other ends of the pair of arms; brackets for supporting the monitor, the brackets being rotatably connected to the connecting member; and means for maintaining the monitor stationary at a certain position by providing the arms and the brackets with a force for restraining the arms and the brackets from being rotated with respect to the base frame and the connecting member against a moment due to a weight of the monitor.

7 Claims, 8 Drawing Sheets

100 162 170 150 170 162a 162 130 R2 R3 170 140a 140 170 121 122 112 120 111 R1

SUPPORTING DEVICE FOR A MONITOR FOR USE IN AN ULTRASONIC DIAGNOSTIC APPARATUS

FIELD OF THE INVENTION

The present invention generally relates to a supporting device for a monitor, and more particularly to a supporting device for a monitor for use in an ultrasonic diagnostic apparatus.

BACKGROUND OF THE INVENTION

An ultrasonic diagnostic apparatus is a medical equipment for obtaining an ultrasound image of a target region in an object so as to provide clinical information of the target region, such as lesion or neoplasm information of internal organs, fetus information and the like.

FIG. 1 shows a general ultrasonic diagnostic apparatus. An ultrasonic diagnostic apparatus 10 comprises the following: a main body 11; a probe 13 for radiating an ultrasonic wave to a target region and receiving an echo signal reflected from the target region; a control panel 12 for operating the apparatus; and a monitor 14 for displaying ultrasound images. To provide convenience to a user, being able to change the position of the monitor is one of the important factors when designing the ultrasonic diagnostic apparatus.

A conventional structure for connecting the monitor 14 to the main body 11 in the ultrasonic diagnostic apparatus 10 is illustrated in FIG. 2. Referring to FIG. 2, a base bracket 11*a* is fixed to the main body 11 and a connecting bar 14*a* is coupled pivotally to the base bracket 11*a* by means of a hinge pin 14*b* at one end. The monitor 14 is coupled pivotally to the other end of the connecting bar 14*a* by means of a hinge pin 14*c*. The monitor 14 can be displaced in a desired position by pivoting the monitor 14 upward or downward in relation to two hinge pins 14*b* and 14*c*. This is so that the user can conveniently inspect the ultrasound image displayed on the monitor 14 in accordance with her or his posture.

After adjusting the position of the monitor 14, the monitor 14 should be kept in the displaced position. Thus, the monitor supporting elements, i.e., the base bracket 11*a*, the connecting bar 14*a* and the hinge pins 14*b* and 14*c*, are engaged with each other in a close fit manner. This is to prevent the monitor 14 from moving freely to an undesired position.

However, in the above prior art supporting structure, as the position of the monitor is adjusted repeatedly, the engagement of the supporting elements becomes loosened due to wear, abrasion or external impact, which causes the monitor to freely move to an undesired position, thereby deteriorating the operational stability. Further, when the supporting elements are coupled to each other too tightly so as to eliminate the above problem, it becomes difficult for the user to be able to move the monitor easily with a small force.

Furthermore, when the elements for restricting the moving range of the monitor are added to the monitor supporting device to prevent the monitor from excessively deviating from the desired position, the monitor and the supporting device cannot be folded flat. Thus, when transporting the ultrasonic diagnostic apparatus, the monitor may bump against other objects (e.g., a wall) and become damaged. Also, when packing the monitor/supporting device assembly, the assembly becomes bulky and will occupy a large space.

SUMMARY OF THE INVENTION

Therefore, it is an object of the present invention to provide a supporting device for a monitor for use in an ultrasonic diagnostic apparatus, which enables a user to displace a monitor easily and diversely according to her or his posture, thereby providing convenience in use.

It is another object of the present invention to provide a supporting device for a monitor for use in an ultrasonic diagnostic apparatus, in which a force for sustaining the monitor can be adjusted simply.

It is yet another object of the present invention to provide a supporting device for a monitor for use in an ultrasonic diagnostic apparatus, which can be folded flat with the monitor, thereby facilitating its transportation and/or packing.

Consistent with the foregoing objects and in accordance with the invention as embodied broadly herein, there is provided a supporting device for a monitor for use in an ultrasonic diagnostic apparatus, which comprises a main body and a monitor installed to the main body for displaying ultrasound images. The supporting device comprises the following: a base frame rotatably mounted to the main body; a pair of arms hingedly jointed to the base frame at respective one ends thereof; a connecting member for interlocking the pair of arms, the connecting member being hingedly coupled to the other ends of the pair of arms; brackets for supporting the monitor, the brackets being rotatably connected to the connecting member; and a device for maintaining the monitor stationary at a certain position by providing the arms and the brackets with a force for restraining the arms and the brackets from being rotated with respect to the base frame and the connecting member against a moment due to a weight of the monitor.

In the present invention, the device for maintaining the monitor stationary includes an elastic pressing member for pressing the arms and the brackets toward the base frame and the connecting member, respectively, to generate a force for restraining the rotation of the arms and the brackets.

The device for maintaining the monitor stationary further includes a compressing member for compressing the elastic pressing member, whereby as the elastic pressing member is compressed, the resilient restoring force of the pressing member increases the force for restraining the rotation of the arms and the brackets.

The supporting device further comprises a device for applying a rotational force to the arms with respect to the base frame against the moment due to the weight of the monitor.

Preferably, the device for applying the rotational force to the arms is a torsion coil spring.

The supporting device further comprises a device for restricting the rotating range of the arms with respect to the base frame.

The device for restricting the rotating range includes a stopper protruding from one of the arms toward the other arm and a shoulder formed at one of the arms near the connecting member. When the stopper contacts the other arm, the rotation of the arms in one direction is stopped. Further, when the shoulder contacts the connecting member, the rotation of the arms in the other direction is stopped.

In addition, there is provided a supporting device for a monitor for use in an ultrasonic diagnostic apparatus, which comprises a main body and a monitor installed to the main body for displaying ultrasound images. The supporting device comprises the following: a base frame rotatably mounted to the main body; a pair of arms hingedly jointed to the base frame at respective one ends thereof by means of hinge shafts; a connecting member for interlocking the pair of arms, the connecting member being hingedly coupled to the other ends of the pair of arms by means of hinge shafts; a supporting shaft coupled to the connecting member; brackets for supporting the monitor, the brackets being rotatably coupled to the supporting shaft; and a device for maintaining the monitor stationary at a certain position by providing the arms and the brackets with a force for restraining the arms and the brackets from being rotated with respect to the base frame and the connecting member against a moment due to a weight of the monitor.

In the present invention, the device for maintaining the monitor stationary includes a spring washer fitted to the hinge shafts and the supporting shaft for pressing the arms and the brackets toward the base frame and the connecting member, respectively, and a nut coupled to the hinge shafts and the supporting shaft. As the nut is tightened, the spring washer is compressed and the resilient restoring force of the spring washer increases a force for restraining the rotation of the arms and the brackets.

Preferably, a torsion coil spring is mounted to the hinge shafts connecting the arms to the base frame. The torsion coil spring provides a rotational force to the arms against the moment due to the weight of the monitor.

BRIEF DESCRIPTION OF DRAWINGS

The above object and features of the present invention will become more apparent from the following description of the preferred embodiments given in conjunction with the accompanying drawings.

DETAILED DESCRIPTION OF THE PRESENT INVENTION

A preferred embodiment of the present invention will now be described with reference to the accompanying drawings.

Figure 3A:
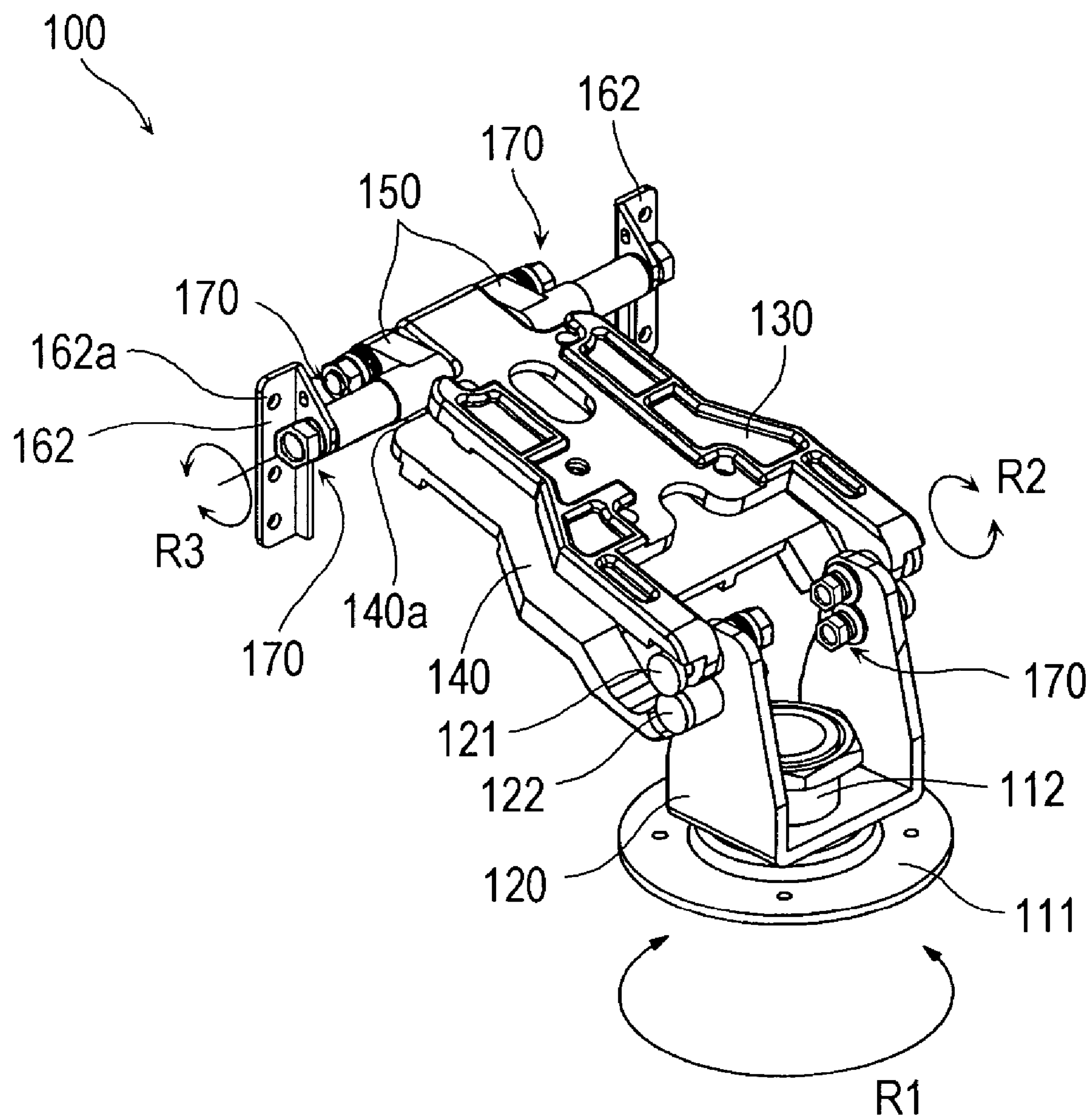
FIG. 3*a* is a top perspective view showing a supporting device for a monitor for use in an ultrasonic diagnostic apparatus constructed in accordance with the present invention.
Figure 3B:
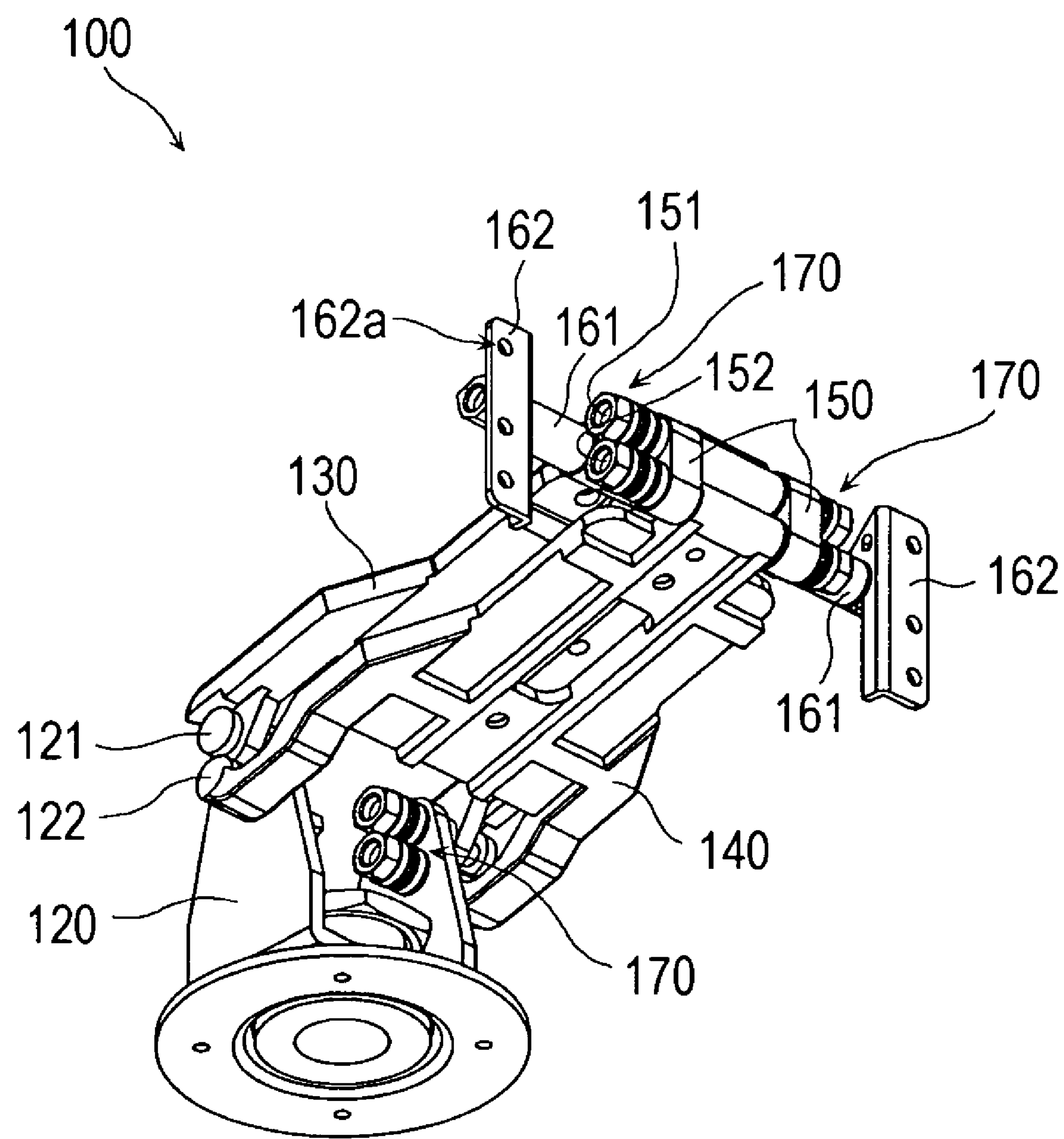
FIG. 3*b* is a bottom perspective view showing the supporting device of FIG. 3*a*.

FIGS. 3*a* and 3*b* are top and bottom perspective views showing a supporting device for a monitor for use in an ultrasonic diagnostic apparatus constructed in accordance with the present invention, respectively.

Figure 1:
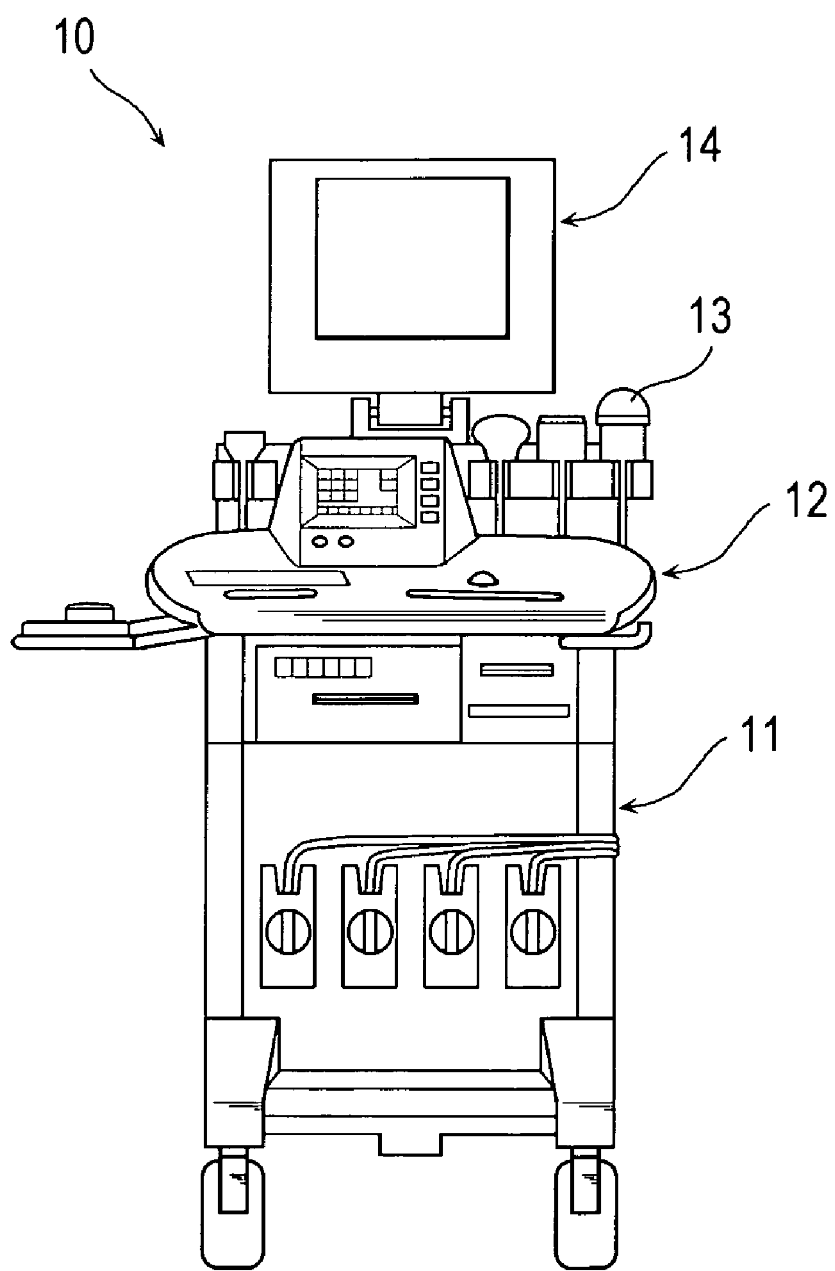
FIG. 1 is a front view showing a general ultrasonic diagnostic apparatus.
Figure 2:
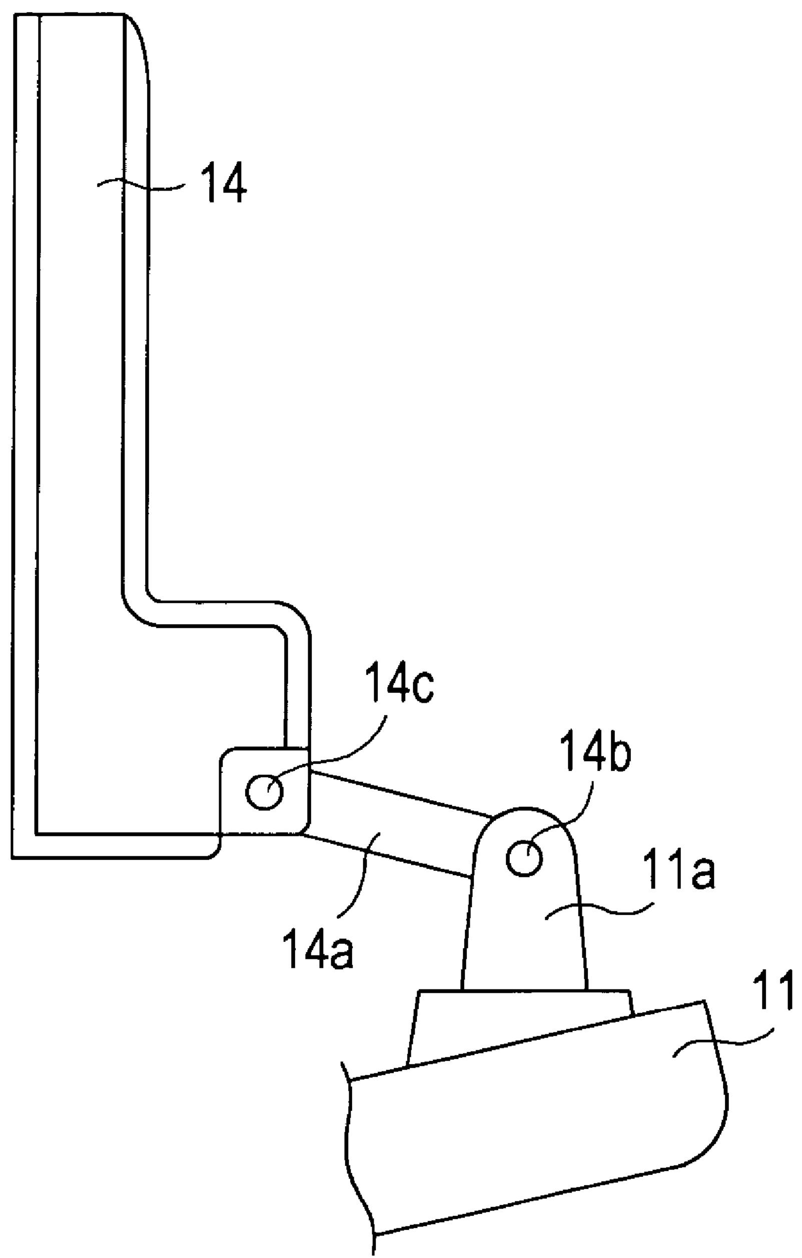
FIG. 2 is a side view showing a supporting structure for a monitor of the prior art.

As shown in the drawings, a plate-shaped mounting bracket 111 is fixed to a main body 11 (see FIG. 1) of an ultrasonic diagnostic apparatus. A base frame 120 is rotatably mounted to the mounting bracket 111 on the axis of a rotating shaft 112. The base frame 120 has a U-shaped cross-section, which has two opposing side walls.

A first arm 130 is hingedly jointed to the side walls of the base frame 120 by means of hinge shafts 121 at one end. A second arm 140 is disposed under the first arm 130 and is hingedly jointed to the side walls of the base frame 120 by means of hinge shafts 122 at one end. Two connecting members 150 are hingedly coupled to the other ends of the first and second arms 130 and 140 by means of hinge shafts 151 and 152, respectively. The other end portions of the arms 130 and 140 are interposed between two connecting members 150.

Two supporting shafts 161 are respectively mounted to the connecting members 150. Each supporting shaft 161 extends outward in parallel with the hinge shafts 121, 122, 151 and 152. A pair of supporting brackets 162 are rotatably mounted to the front end portions of the supporting shafts 161. The monitor 14 (see FIG. 1) can be fixed to the brackets 162 by fastening screws into a case of the monitor 14 through screw holes 162*a* of the brackets 162.

Through the above monitor supporting device 100, the monitor 14 can be moved in a multiple degree-of-freedom. More specifically, the monitor 14 can be displaced in a direction of double-headed arrow R1 on the axis of the rotating shaft 112, in a direction of double-headed arrow R2 on the axis of the hinge shafts 121 and 122, and in a direction of double-headed arrow R3 on the axis of the supporting shafts 161.

The supporting device 100 further comprises a device 170 for maintaining the monitor 14 stationary after being displaced to a desired position. The device 170 is mounted to the supporting shafts 161 and at least one of the hinge shafts 121, 122, 151 and 152. The device 170 prevents the monitor 14 from being undesirably displaced from the position set by the user.

Figure 4:
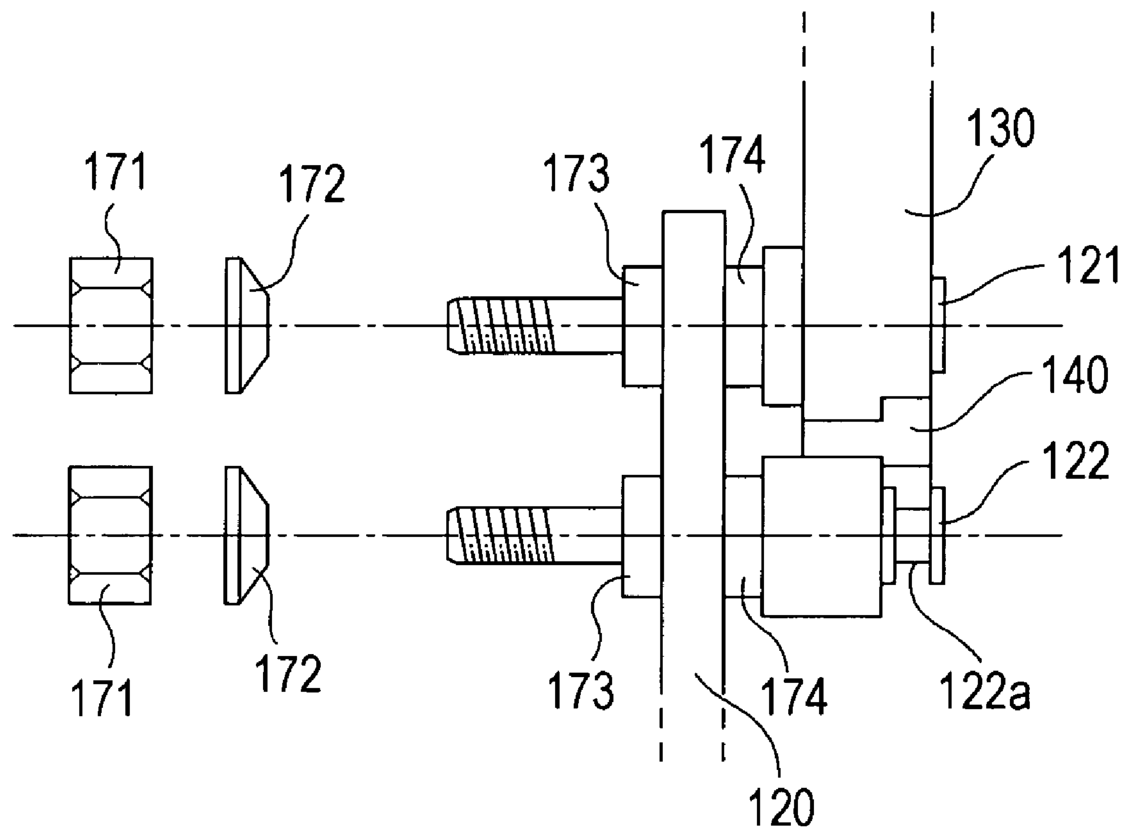
FIG. 4 is an enlarged front view showing a coupling structure of arms, hinge shafts and a device for maintaining a monitor stationary.

Referring to FIG. 4, each of the device 170 for maintaining the monitor 14 stationary includes: flat washer 173 fitted to each shaft 121, 122, 151, 152 and 161; an elastic pressing member 172 fitted to each shaft next to the flat washer 173; and a nut 171 screw-coupled to each shaft next to the elastic pressing member 172. When the device 170 is applied to the hinge shaft 121 or 122, the device 170 further includes another flat washer 174 fitted to the hinge shaft 121 or 122 such that the flat washer 174 is interposed between the base frame 120 and the first or second arm 130 or 140. The flat washer 173 is located on the opposite side of the base frame 120 to the flat washer 174. The elastic pressing member 172 may be one of the members capable of applying a pressing force to the flat washer 173 along the axial direction of the shaft. In this embodiment, the elastic pressing member 172 is a spring washer.

As the nut 171 becomes tightened, the spring washer 172 is compressively deformed and the resilient restoring force of the spring washer 172 is applied to the flat washer 173 to push the same toward the base frame 120. Because the hinge shaft 121 or 122 is provided with a head portion at one end so as to be prevented from being separated from the first or second arm 130 or 140, the flat washers 173 and 174, the base frame 120 and the first or second arm 130 or 140 are placed in close contact with each other. The more the nut 171 is tightened, the larger the static frictional force between the first or second arm 130 or 140 and the flat washer 174 becomes. Accordingly, in some cases, if the nut 171 is tightened to the maximum, the monitor 14 cannot be displaced, but is fixed at one position.

When the user applies a force to the monitor 14 to change its position, the force produces a torque. If the torque is larger than the static frictional force between the first or second arm 130 or 140 and the flat washer 174, the first or second arm 130 or 140 is rotated about the hinge shaft 121 or 122. After the force is removed from the monitor 14, the moment due to the weight of the monitor 14 is applied to the arms 130 and 140. Therefore, it is preferable that the static frictional force between the first or second arm 130 or 140 and the flat washer 174 is set to be equal to or slightly larger than the moment due to the weight of the monitor 14. This is so that the monitor 14 can be maintained in a stationary position. As described above, the static frictional force can be easily adjusted by the extent to which the nut 171 is tightened.

If the device 170 for maintaining the monitor 14 stationary is mounted to both the hinge shaft 121 of the first arm 130 and the hinge shaft 122 of the second arm 140, the extent of tightening the nut 171 of each hinge shaft will be half of that when the device 170 is mounted to only one hinge shaft.

Referring now back to FIGS. 3*a* and 3*b*, the device 170 for maintaining the monitor 14 stationary, which includes the flat washer, the elastic pressing member and the nut, may be additionally mounted to the hinge shafts 151 and 152. This is to intensify the static frictional force against the moment due to the weight of the monitor 14.

Further, the device 170 for maintaining the monitor 14 stationary is also mounted to the supporting shafts 161, to which the supporting brackets 162 are rotatably mounted. By tightening the nut, the static frictional force between the device 170 and the supporting brackets 162 is adjusted so that the supporting brackets 162 are prevented from being undesirably rotated about the supporting shafts 161 by the moment due to the weight of the monitor 14.

Figure 5:
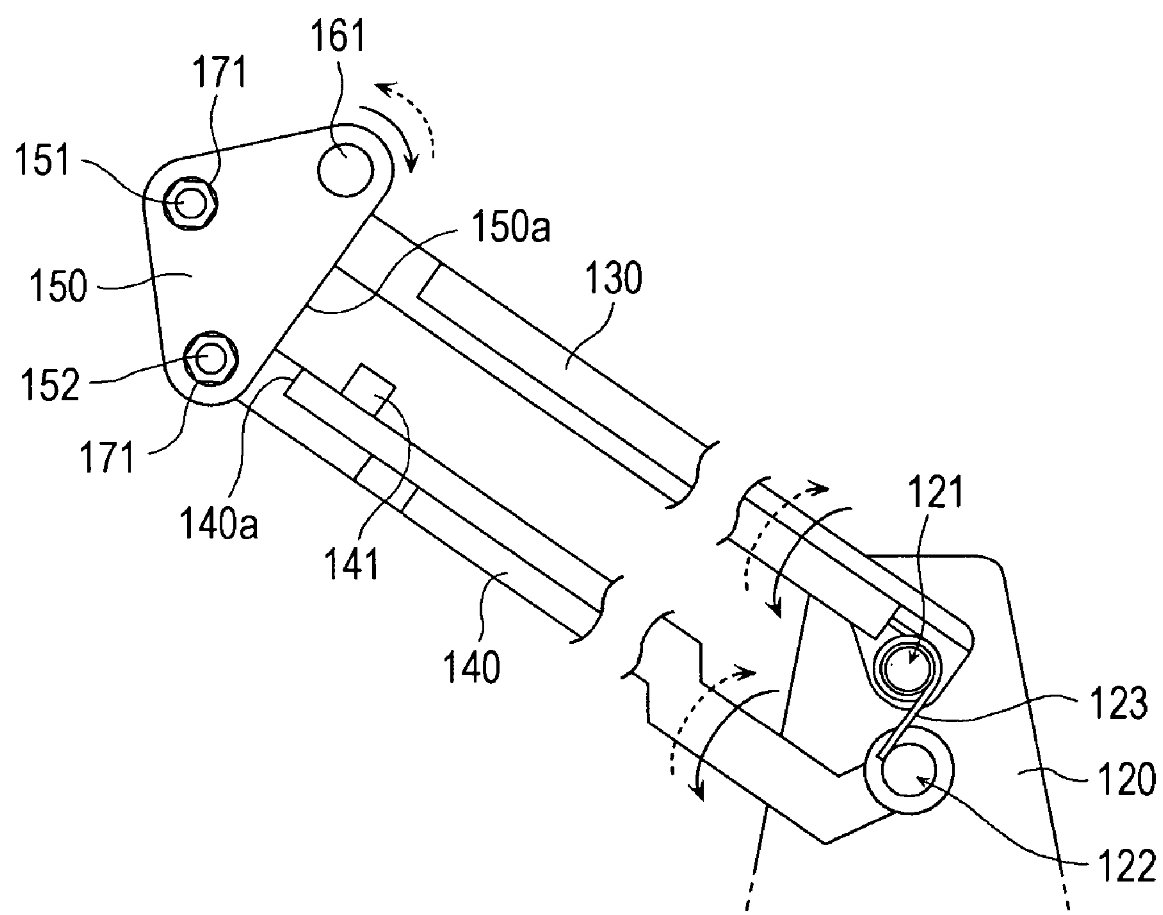
FIG. 5 is an enlarged side view showing an operating state of the supporting device constructed in accordance with the present invention.

FIG. 5 is an enlarged side view showing an operating state of the supporting device constructed in accordance with the present invention.

As shown in the drawing, when the first and second arms 130 and 140 are rotated together counterclockwise about the hinge shafts 121 and 122 with respect to the base frame 120, the connecting member 150 is rotated clockwise (as shown by real-line arrows). In such a case, the distance between the first arm 130 and the second arm 140 becomes wider. This rotational operation is not restricted until a contacting surface 150*a* of the connecting member 150 comes in contact with a shoulder 140*a* (see FIG. 3*a*) of the second arm 140.

On the contrary, when the first and second arms 130 and 140 are rotated together clockwise about the hinge shafts 121 and 122, the connecting member 150 is rotated counterclockwise (as shown by dotted arrows). In such a case, the distance between the first arm 130 and the second arm 140 becomes narrower. This rotational operation is not restricted until a stopper 141, which protrudes toward the first arm 130 from the second arm 140, comes in contact with the first arm 130.

The rotating angle of the first and second arms 130 and 140 with respect to the base frame 120 can be determined in accordance with the shape, the location or the like of the shoulder 140*a* and the stopper 141. The device for restricting the rotational range of the arms 130 and 140 is not limited to the shoulder 140*a* and the stopper 141, which are illustrated in FIG. 5.

The supporting device 100 of the present invention further comprises a device for enabling the user to move the monitor 14 upward with a relatively small force. More specifically, when the user intends to move the monitor 14 downward, the user may pull down the monitor 14 with a force equivalent to a difference just between the above-described static frictional force and the moment due to the weight of the monitor 14. However, when the user intends to move the monitor 14 upward, the user should push up the monitor 14 with a larger force against the static frictional force and the moment due to the weight of the monitor 14. In order to relieve the user from this problem, a torsion coil spring 123 is provided at the hinge shaft 121 of the first arm 130. Two end portions of the torsion coil spring 123 extend angle-wise with respect to each other. One end portion is placed in a groove (not shown) formed at the first arm 130 in the vicinity of the hinge shaft 121. The other end portion is placed in a groove 122*a* (see FIG. 4) formed on the peripheral surface of the hinge shaft 122 of the second arm 140. If the first and second arms 130 and 140 are rotated counterclockwise about the hinge shafts 121 and 122, the torsion coil spring 123 is compressed such that its two end portions become narrower. Therefore, the reaction resilient energy is stored in the torsion coil spring 123. As a result, when the user pushes up the monitor 14 (i.e., when the first and second arms 130 and 140 are rotated clockwise), the resilient energy stored in the torsion coil spring 123 helps the user to easily move the monitor 14 upward.

Figure 6:
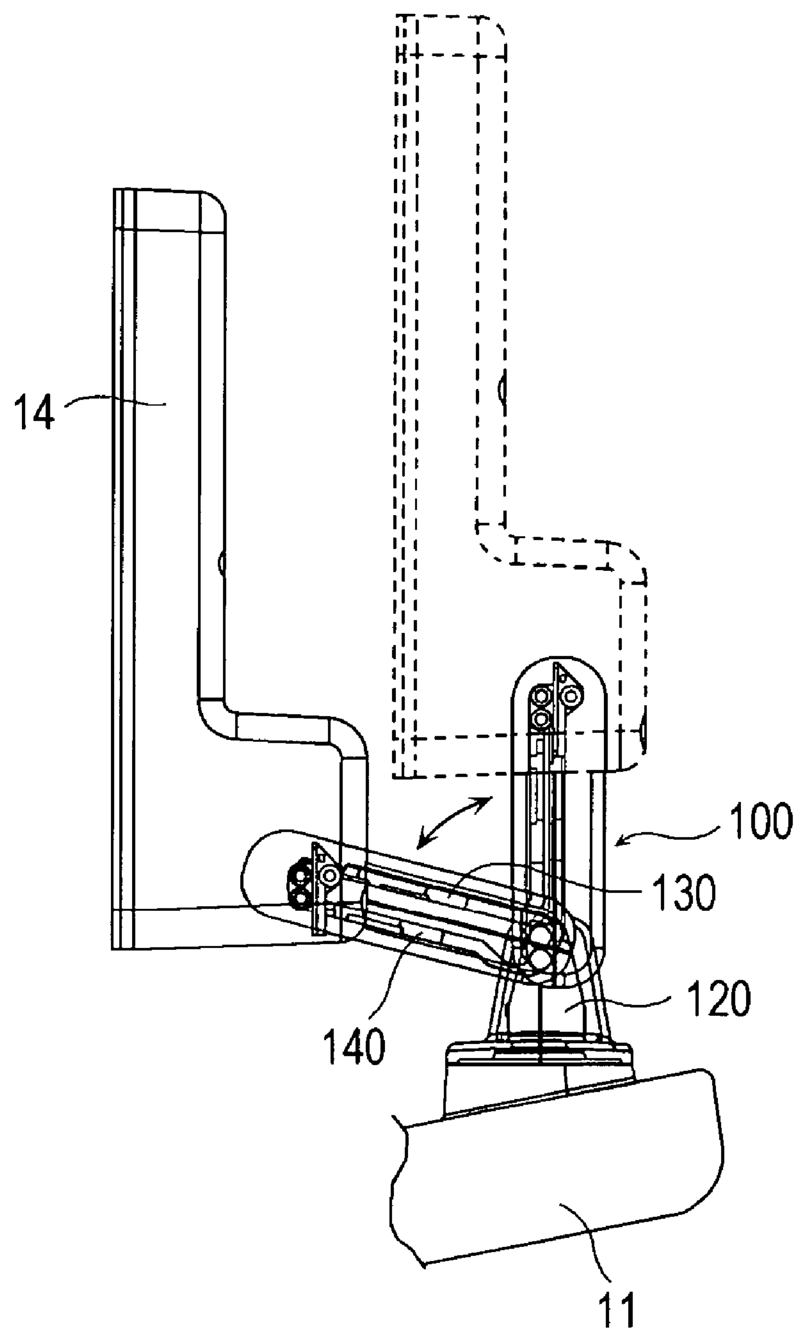
FIG. 6 is a side view showing a displacement of a monitor.
Figure 7:
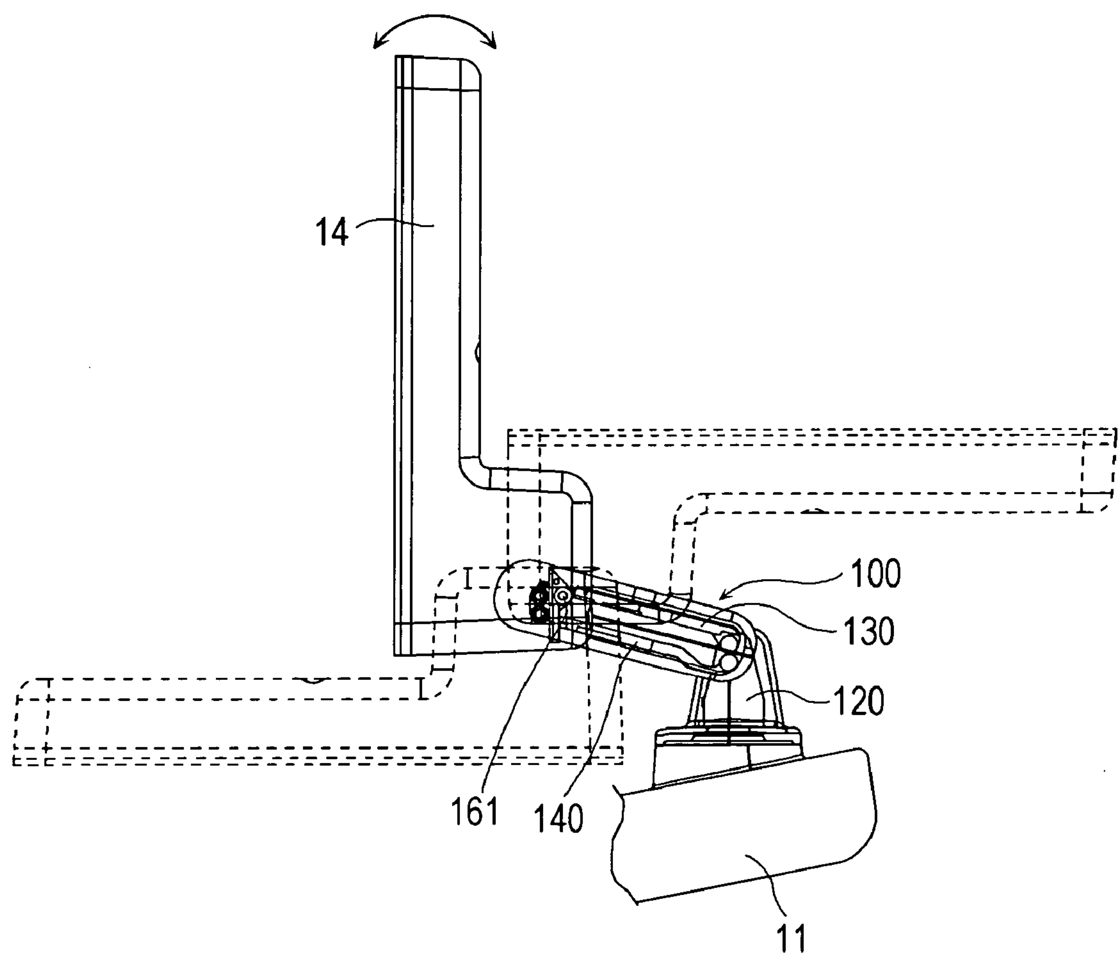
FIG. 7 is a side view showing another displacement of a monitor.

FIGS. 6 and 7 are side views showing various displacements of the monitor 14. As shown in FIG. 6, the monitor 14 can be moved upward or downward by the rotation of the first and second arms 130 and 140 with respect to the base frame 120. In addition, as shown in FIG. 7, the monitor 14 can be rotated about the supporting shaft 161 with respect to the arms 130 and 140. Particularly, since the monitor 14 can be rotated with an angle of 180° or more on the axis of the supporting shaft 161, it can be folded flat with the supporting device 100.

As described above in detail, the monitor supporting device according to the present invention enables a user to displace a monitor easily and diversely according to his or her posture by adopting a multi-joint structure, thereby providing convenience in use.

Also, the force for sustaining the monitor can be simply adjusted merely by tightening or loosening a nut provided at hinge shafts.

Further, since the monitor can be folded flat with the supporting device, the packing and transporting can be facilitated.

While the present invention has been described and illustrated with respect to a preferred embodiment of the invention, it will be apparent to those skilled in the art that variations and modifications are possible without deviating from the broad principles and teachings of the present invention which should be limited solely by the scope of the claims appended hereto.

What is claimed is:

1. A supporting device for a monitor for use in an ultrasonic diagnostic apparatus having a main body and a monitor installed to the main body for displaying ultrasound images, the supporting device comprising:

a base frame rotatably mounted to the main body and including two opposing side walls;

a first arm hingedly jointed at one end thereof to each of the side walls by means of hinge shafts;

a second arm disposed under the first arm and being hingedly jointed at one end thereof to each of the side walls by means of hinge shafts;

two connecting member for interlocking the first and second arms, each of the connecting members being hingedly coupled to the other end of the first arm and the other end of the second arm by means of hinge shafts, the other ends of the first and second arms being interposed between the connecting members;

two supporting shafts mounted to the connecting members, respectively, and extending in parallel with the hinge shafts;

a pair of brackets for supporting the monitor, the brackets being rotatably mounted to the supporting shafts, respectively, the monitor being fixed to the brackets; and means for maintaining the monitor stationary at a certain position by providing the arms and the brackets with a force for restraining the arms and the brackets from being rotated with respect to the base frame and the connecting member against a moment due to a weight of the monitor, wherein the means for maintaining the monitor stationary includes a spring washer fitted to the hinge shafts and the supporting shafts for pressing the arms and the brackets toward the base frame and the connecting member, respectively, to generate a force for restraining the rotation of the arms and the brackets, and a nut coupled to the hinge shafts and the supporting shafts for compressing the spring washer, wherein as the nut is tightened, the spring washer is compressed and the resilient restoring force of the spring washer increases the force for restraining the rotation of the arms and the brackets.

2. The supporting device of claim 1, wherein the supporting device further comprises means for applying a rotational force to the arms with respect to the base frame against the moment due to the weight of the monitor.

3. The supporting device of claim 2, wherein the means for applying the rotational force to the arms is a torsion coil spring.

4. The supporting device of claim 1, wherein the supporting device further comprises means for restricting the rotating range of the arms with respect to the base frame.

5. The supporting device of claim 4, wherein the means includes a stopper protruding from one of the arms toward the other arm and a shoulder formed at one of the arms near the connecting member, whereby when the stopper contacts the other arm, the rotation of the arms in one direction is stopped, and whereby when the shoulder contacts the connecting member, the rotation of the arms in the other direction is stopped.

6. The supporting device of claim 3, wherein the torsion coil spring is mounted to the hinge shaft connecting one of the arms to the base frame, the torsion coil spring providing a rotational force to the arms against the moment due to the weight of the monitor.

7. The supporting device of claim 1, wherein the nut coupled to the hinge shafts and the supporting shafts for compressing the spring washer is an adjustable nut.

* * * * *